US011400198B2

(12) United States Patent
Tal

(10) Patent No.: US 11,400,198 B2
(45) Date of Patent: Aug. 2, 2022

(54) HEMODIALYSIS CATHETER WITH CORRUGATED TIPS

(71) Applicant: PRISTINE ACCESS TECHNOLOGIES LTD, Tel-Aviv (IL)

(72) Inventor: Michael Gabriel Tal, Savyon (IL)

(73) Assignee: Pristine Access Technologies Ltd., Tel-Aviv (IL)

(*) Notice: Subject to any disclaimer, the term of this patent is extended or adjusted under 35 U.S.C. 154(b) by 520 days.

(21) Appl. No.: 15/745,353

(22) PCT Filed: Jul. 20, 2016

(86) PCT No.: PCT/IB2016/054317
§ 371 (c)(1),
(2) Date: Jan. 16, 2018

(87) PCT Pub. No.: WO2017/013598
PCT Pub. Date: Jan. 26, 2017

(65) Prior Publication Data
US 2018/0207347 A1    Jul. 26, 2018

Related U.S. Application Data

(60) Provisional application No. 62/194,325, filed on Jul. 20, 2015.

(51) Int. Cl.
*A61M 1/36* (2006.01)
*A61M 25/00* (2006.01)

(52) U.S. Cl.
CPC ........ *A61M 1/3661* (2014.02); *A61M 25/003* (2013.01); *A61M 25/0068* (2013.01); *A61M 2025/0031* (2013.01)

(58) Field of Classification Search
CPC ............ A61M 1/3661; A61M 25/0068; A61M 25/003; A61M 2025/0031;
(Continued)

(56) References Cited

U.S. PATENT DOCUMENTS 5,156,592 A    10/1992 Martin et al.
5,800,414 A    9/1998 Cazal
(Continued)

FOREIGN PATENT DOCUMENTS

EP    1610853 A1    1/2006
EP    1792637 A2    6/2007
(Continued)

OTHER PUBLICATIONS

Nov. 15, 2016 International Search Report issue in International Application No. PCT/IB2016/054317.

*Primary Examiner* — Nicholas J. Weiss
*Assistant Examiner* — Alessandro R Del Priore
(74) *Attorney, Agent, or Firm* — Rutan & Tucker LLP

(57) ABSTRACT

Hemodialysis catheter with corrugated tips. Includes elongated body having first and second distal end regions terminating in tips opened to lumens extending continuously along both elongated body and distal end regions. Each tip includes a tip edge extending from tip tubular wall and surrounding tip opening. Each tip tubular wall has a corrugated configuration with at least two grooves, including outer and inner grooves, merging into the tip edge. Grooves may have same or different lengths, widths, or/and spatial configurations. Distal end regions may be elastic and configured to have non-stressed form when divergent, via diverging angles, from elongated body longitudinal axis, and may be rotationally symmetric relative to the axis. In some embodiments, tip inner wall and hollow outer surfaces merge into a corrugated form having alternating grooves and ridges along distal ends of the tip, that enable the catheter to facilitate active lateral or frontal fluid traversability therethrough.

15 Claims, 6 Drawing Sheets

(58) Field of Classification Search
CPC ...... A61M 25/0071; A61M 2025/0037; A61M 25/0029; A61M 25/0026; A61M 2025/0034; A61M 1/3659; A61M 1/3653; A61M 39/08; A61M 25/0032; A61M 25/10; A61M 25/007

See application file for complete search history.

(56) References Cited

U.S. PATENT DOCUMENTS

| | | |
|---|---|---|
| 5,947,953 A | 9/1999 | Ash et al. |
| 6,001,079 A | 12/1999 | Pourchez |
| 6,482,169 B1 | 11/2002 | Kuhle |
| 6,513,527 B1 | 2/2003 | Abdel-aziz |
| 7,108,674 B2 | 9/2006 | Quinn |
| 7,182,746 B2 | 2/2007 | Haarala et al. |
| 7,776,005 B2 | 8/2010 | Haggstrom et al. |
| 8,066,660 B2 | 11/2011 | Gregersen et al. |
| 8,092,415 B2 | 1/2012 | Moehle et al. |
| 2002/0052641 A1 | 5/2002 | Monroe et al. |
| 2002/0062129 A1 | 5/2002 | Mikus et al. |
| 2003/0153898 A1 | 8/2003 | Schon et al. |
| 2004/0087892 A1* | 5/2004 | Cunningham .... A61M 25/0043 604/43 |
| 2004/0092863 A1 | 5/2004 | Raulerson et al. |
| 2004/0167463 A1 | 8/2004 | Zawacki et al. |
| 2004/0172003 A1* | 9/2004 | Wilson .............. A61M 25/0097 604/508 |
| 2005/0054989 A1 | 3/2005 | McGuckin et al. |
| 2005/0277862 A1 | 12/2005 | Anand |
| 2006/0025781 A1 | 2/2006 | Young et al. |
| 2006/0149350 A1 | 7/2006 | Patel et al. |
| 2007/0208276 A1 | 9/2007 | Volk et al. |
| 2007/0225661 A1* | 9/2007 | Ash ................... A61M 25/0032 604/284 |
| 2009/0137944 A1 | 5/2009 | Haarala et al. |
| 2009/0204052 A1* | 8/2009 | Nimkar ............. A61M 25/0026 604/523 |
| 2009/0204079 A1 | 8/2009 | Nimkar et al. |
| 2009/0209940 A1 | 8/2009 | Nimkar et al. |
| 2011/0011525 A1 | 1/2011 | Sanscoucy |
| 2011/0196190 A1* | 8/2011 | Farnan ................ A61M 60/148 604/103.08 |
| 2012/0130392 A1 | 5/2012 | Levy et al. |
| 2012/0143123 A1 | 6/2012 | Agnew |
| 2012/0179102 A1 | 7/2012 | Blanchard et al. |
| 2013/0324964 A1* | 12/2013 | Florescu .......... A61M 25/0032 604/523 |
| 2014/0261407 A1* | 9/2014 | Roberts ................ A61M 39/10 128/202.16 |

FOREIGN PATENT DOCUMENTS

| | | |
|---|---|---|
| EP | 1610853 B1 | 5/2009 |
| EP | 2277579 A1 | 1/2011 |
| EP | 2446915 B1 | 1/2018 |
| WO | 9115255 A1 | 10/1991 |
| WO | 1997009086 A1 | 3/1997 |
| WO | 2003045464 A2 | 6/2003 |
| WO | 2004096334 A1 | 11/2004 |
| WO | 2014197614 A2 | 12/2014 |
| WO | WO-2014197614 A2 * | 12/2014 ........ A61M 25/0029 |

\* cited by examiner

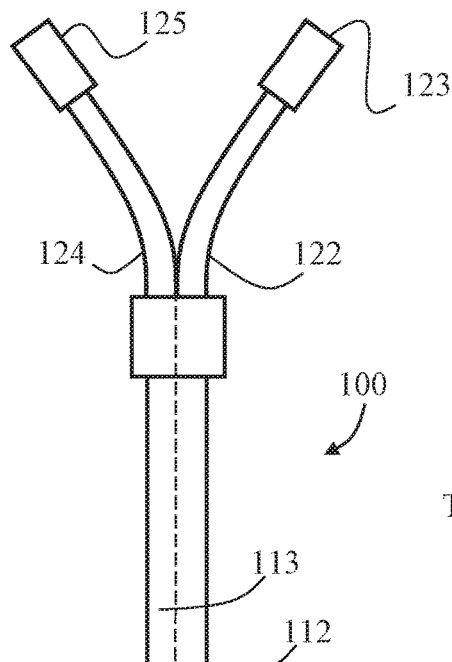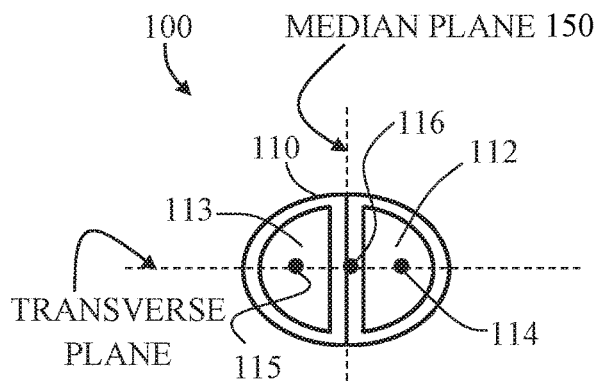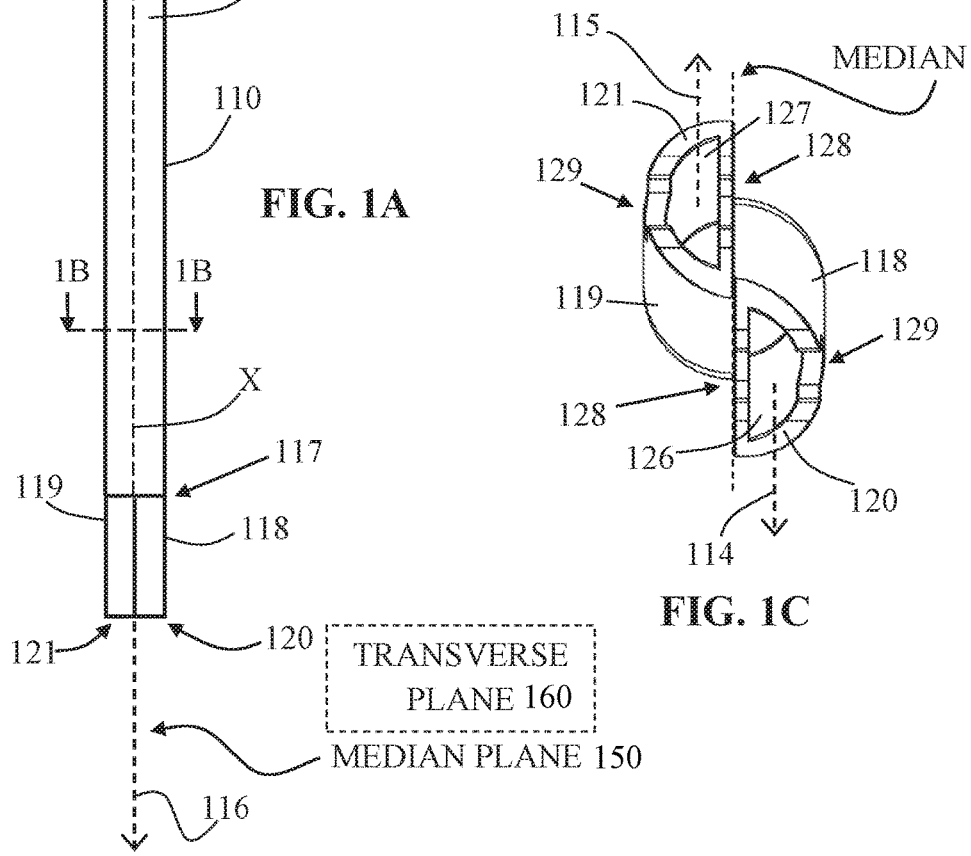

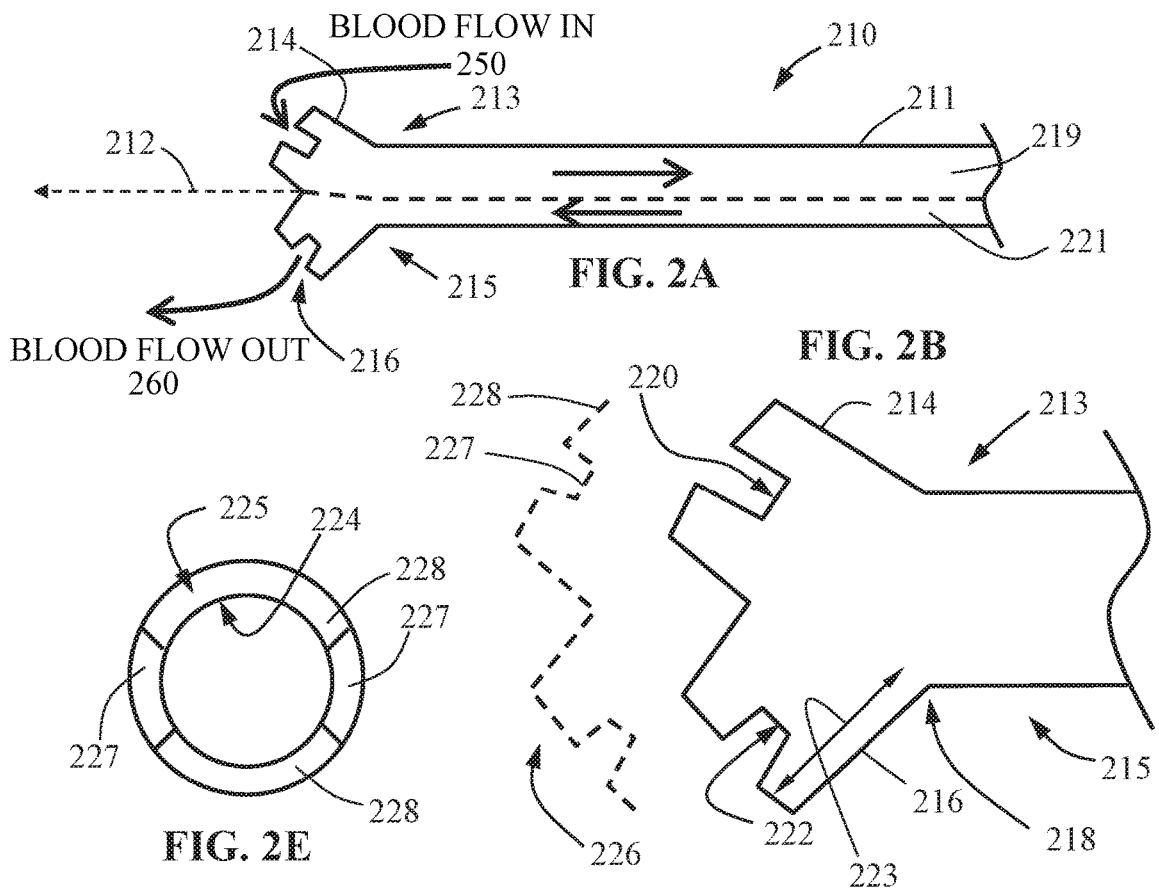
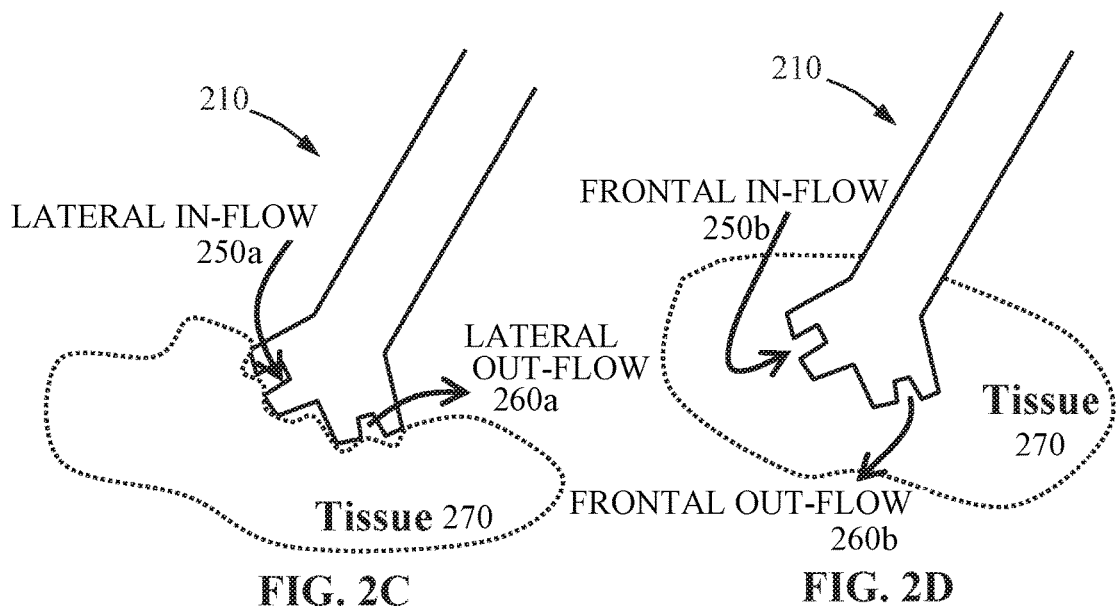

HEMODIALYSIS CATHETER WITH CORRUGATED TIPS

RELATED APPLICATIONS

This application is a U.S. National Stage Entry Under 35 U.S.C. 371 of International Application No. PCT/IB2016/054317 filed on Jul. 20, 2016, which claims the benefit of priority under 35 USC 119(e) of U.S. Provisional Patent Application No. 62/194,325, filed 20 Jul. 2015, entitled "Hemodialysis Catheter with A Corrugated Distal End". The contents of the above applications are incorporated herein by reference in their entireties.

FIELD OF THE INVENTION

The present invention, in some embodiments thereof, relates to medical catheter apparatuses, and more particularly, but not exclusively, to dialysis catheters having a dual or split tip.

BACKGROUND OF THE INVENTION

Dual or split tip dialysis catheters are currently mostly employed for chronic use of exchanging blood to and from a subject and a hemodialysis machine. During an exemplary hemodialysis procedure, a multiple lumen catheter is inserted into the subject's body and blood is withdrawn through an arterial lumen of the catheter. This blood is supplied to a hemodialysis machine which dialyzes, or cleans, the blood to remove waste and excess water. The dialyzed blood is returned to the subject through a venous lumen of the catheter. Flow in the catheter may need to be reversed from time to time, so that blood will flow in opposite directions in both the arterial lumen and venous lumen as mentioned above.

Flow occlusion is a major cause of concern, and possible problems, when treating subjects via hemodialysis, due to high flow rates and high blood recirculation pressures involved in a relatively small space within a dialysis hosting blood system. Flow occlusion primarily occurs due to blockage of the arterial lumen, either due to immediate positional occlusion when catheter openings are covered or submerged in surrounding tissue, or/and due to longer term bodily reaction to artifact presence. Common causes of long term occlusions are fibrin sheath formation, and thrombus formation. With positional occlusion of the catheter, for example, a tip of the catheter has, to some extent, freedom of movement inside the subject, and this can cause occlusion, as a tip of the catheter or a side hole may be sucked against a blood vessel or heart wall.

PCT Int'l. Appl. Pub. No. WO 2014/197614 A2, of same applicant/assignee as the present invention, teaches about a dual (split) tip dialysis catheter, which includes a proximal portion with connected lumens, and a distal portion with diverging lumens. The lumens may separate at a split junction and diverge in a scissors like manner to reduce or eliminate a crack or gap adjacent to the split junction, thereby reducing clotting. Such a dual or split tip dialysis catheter may have forward openings configured to direct flow in opposite directions.

Additional exemplary teachings in the field and art of the invention are disclosed in: U.S. Pat. Nos. 5,800,414; 5,947,953; 7,108,674; 7,182,746; 7,776,005; 8,066,660; and 8,092,415.

In spite of extensive teachings in the field and art of hemodialysis catheters, and in view of various significant limitations and potential problems associated with such teachings, for example, as explained above, there is an on-going need for developing and implementing improved or/and new hemodialysis catheters that are effective in preventing, or at least diminishing, blockage of hemodialysis lumens and blood recirculation openings associated with hemodialysis treatment systems.

SUMMARY OF THE INVENTION

The present invention, in some embodiments thereof, relates to medical catheter apparatuses, and more particularly, but not exclusively, to dialysis catheters having a dual or split tip. In exemplary embodiments of the present invention, the herein disclosed dialysis catheter corresponds to a dual (split) tip hemodialysis catheter having corrugated tips.

In exemplary embodiments, the hemodialysis catheter includes an elongated body extending along a longitudinal axis, first and second distal end regions terminating in first and second tips opened to first and second lumens that continuously extend along both the elongated body and the respective first and second distal end regions. Each tip includes a tip edge extending from tip tubular wall and surrounding tip opening. Each tip tubular wall is part of a corrugated configuration, and has at least two grooves, including outer and inner grooves, merging into the tip edge. Grooves may have same or different lengths, widths, or/and spatial configurations. Distal end regions may be elastic and configured to have a non-stressed form when divergent, via diverging angles, from the elongated body longitudinal axis. Distal end regions may be rotationally symmetric relative to the longitudinal axis. Distal end regions may be separated from each other along a splitting plane adjacent to a junction, optionally, a median plane adjacent to the junction and perpendicular to the longitudinal axis. Distal end regions may be parallel to the splitting plane.

In exemplary embodiments, when the hemodialysis catheter is in a non-stressed form, the tip openings are oriented in opposite directions relative to each other and away from the longitudinal axis. In exemplary embodiments, each tip includes a tip extension, an inner wall surface extending along the tip extension, and a hollow outer surface, whereby the inner wall surface and the hollow outer surface merge into a corrugated form having alternating grooves and ridges along the distal end of the tip extension. When the hollow outer surface is fully covered and the inner wall surface is at least partially uncovered, the hemodialysis catheter facilitates active lateral fluid traversability therethrough. When the hollow outer surface is at least partially uncovered and the inner wall surface is fully covered, the hemodialysis catheter facilitates active frontal fluid traversability therethrough.

In exemplary embodiments of the present invention, the hemodialysis catheter with corrugated tips includes particular structural features that are effective in preventing, or at least diminishing, blockage of hemodialysis lumens and blood recirculation openings associated with employing hemodialysis treatment systems. Such effectiveness may be highly advantageous compared to, and solve problems associated with, known hemodialysis catheters and uses thereof.

According to an aspect of some embodiments of the present invention, there is provided a hemodialysis catheter, comprising an elongated body extending along a longitudinal axis, a first distal end region terminating in a first tip opened to a first lumen extending continuously along both the elongated body and the first distal end region, and a second distal end region terminating in a second tip opened to a second lumen extending continuously along both the elongated body and the second distal end region; wherein the first tip includes a first tip edge extending from a first tip tubular wall and surrounding a first tip opening, and the second tip includes a second tip edge extending from a second tip tubular wall and surrounding a second tip opening; wherein the first tip tubular wall includes at least two grooves merging into the first tip edge, including a first outer groove and a first inner groove, and the second tip tubular wall includes at least two grooves merging into the second tip edge, including a second outer groove and a second inner groove.

According to some embodiments of the invention, the first inner groove extends along a first inner side of the first distal end region and the second inner groove extends along a second inner side of the second distal end region, wherein the first inner side at least partially contacts the second inner side. According to some embodiments of the invention, the first inner groove opposes the first outer groove or/and the second inner groove opposes the second outer groove. According to some embodiments of the invention, the first inner groove has length equal to length of the first outer groove or/and the second inner groove has length equal to length of the second outer groove. According to some embodiments of the invention, the first inner groove has length greater than length of the first outer groove or/and the second inner groove has length greater than length of the second outer groove. According to some embodiments of the invention, the first inner groove has length less than length of the first outer groove or/and the second inner groove has length less than length of the second outer groove.

According to some embodiments of the invention, each of the at least two grooves of the first and second tip tubular walls has length of at least 2 mm, optionally, particularly, in a range of between 2 mm and 3 mm. According to some embodiments of the invention, each of the at least two grooves of the first and second tip tubular walls has width of at least 1 mm, optionally, particularly, in a range of between 1 mm and 1.5 mm.

According to some embodiments of the invention, at least one of the first and second distal end regions is elastic and configured to have a non-stressed form when the first distal end region diverges from the longitudinal axis via a first diverging angle or/and the second distal end region diverges from the longitudinal axis via a second diverging angle. According to some embodiments of the invention, the first diverging angle is equal and directionally opposite to the second diverging angle, relative to the longitudinal axis, thereby forming together a total diverging angle defined by and spanning between the first and second distal end regions. According to some embodiments of the invention, the total diverging angle is in a range of between 5° and 50°, optionally, particularly, between 20° and 30°. According to some embodiments of the invention, the first inner groove is convergent with, or crosses, the second inner groove when the first and second distal end regions are aligned with the longitudinal axis.

According to some embodiments of the invention, the first inner groove is fully separated from the second inner groove when at least one of the first and second distal end regions is in the non-stressed form. According to some embodiments of the invention, the first and second distal end regions, and, the first and second inner grooves, are rotationally symmetric relative to the longitudinal axis.

According to some embodiments of the invention, the first and second distal end regions are separated from each other along a splitting plane adjacent to a junction, optionally, a median plane adjacent to the junction and perpendicular to the longitudinal axis. According to some embodiments of the invention, the first and second distal end regions are parallel to the splitting plane. According to some embodiments of the invention, the first tip tubular wall has a first flat surface and the second tip tubular wall has a second flat surface facing the first flat surface. According to some embodiments of the invention, at least one of the first flat surface and the second flat surface is parallel to the splitting plane.

According to some embodiments of the invention, at least one of the first inner groove and the first outer groove is in a form of a straight slit extending parallel to long axis of the first distal end portion, and at least one of the second inner groove and the second outer groove is in a form of a straight slit extending parallel to long axis of the second distal end portion.

According to some embodiments of the invention, relative to the junction, the first tip has an extension length equal to extension length of the second tip. According to some embodiments of the invention, the first and second tips have a blunt form.

According to some embodiments of the invention, the hemodialysis catheter comprises removable aligning means that facilitate alignment of the first distal end region together with the second distal end region to the longitudinal axis, wherein upon removal of the aligning means, the first distal end region and the second distal end region slide against each other under elastic stresses, according to a scissor-like movement, along the splitting plane, whereby the first and second distal end regions revert back to a non-stressed form.

According to some embodiments of the invention, the first lumen and the second lumen are independent from each other, so as to facilitate simultaneous and oppositely directed flow through the first and second lumens.

According to some embodiments of the invention, the first lumen has a first tip longitudinal axis extending along a center thereof, and the second lumen has a second tip longitudinal axis extending along a center thereof, wherein, when the catheter is in a non-stressed form, the first and second tip longitudinal axes of the lumens are parallel along a proximal portion of the catheter and diverge along a distal portion of the catheter.

According to some embodiments of the invention, the first and second tip longitudinal axes define a splitting plane being a transverse plane including both of the first and second tip longitudinal axes in the proximal portion of the catheter.

According to some embodiments of the invention, the first inner groove and the first outer groove are positioned 180 degrees circumferentially away from each other relative to the first tip longitudinal axis, or/and the second inner groove and the second outer groove are positioned 180 degrees circumferentially away from each other relative to the second tip longitudinal axis.

According to some embodiments of the invention, one of the first inner groove and the first outer groove is positioned closer than the other to the longitudinal axis, or/and one of the second inner groove and the second outer groove is positioned closer than the other to the longitudinal axis. According to some embodiments of the invention, each of the first and second tips diverges from the elongated body and has a protrusion length in a range of between 5 mm and 35 mm, optionally, particularly, in a range of between 10 mm and 15 mm.

According to an aspect of some embodiments of the present invention, there is provided a hemodialysis catheter, comprising an elongated body extending along a longitudinal axis, a first distal end region terminating in a first tip, and a second distal end region terminating in a second tip, the first and second distal end regions being separated from each other along a splitting plane adjacent a junction; wherein the first distal end region encloses a first lumen opened to a first tip opening provided at the first tip, and the second distal end region encloses a second lumen opened to a second tip opening provided at the second tip; wherein, when the hemodialysis catheter is in a non-stressed form, the first and second tip openings are oriented in opposite directions relative to each other and away from the longitudinal axis; wherein each of the first and second tips includes a tip extension, an inner wall surface extending along the tip extension, and a hollow outer surface, the inner wall surface and the hollow outer surface merge into a corrugated form having alternating grooves and ridges along distal end of the tip extension; wherein, when the hollow outer surface is fully covered and the inner wall surface is at least partially uncovered, the hemodialysis catheter facilitates active lateral fluid traversability therethrough; and wherein, when the hollow outer surface is at least partially uncovered and the inner wall surface is fully covered, the hemodialysis catheter facilitates active frontal fluid traversability therethrough.

All technical or/and scientific words, terms, or/and phrases, used herein have the same or similar meaning as commonly understood by one of ordinary skill in the art to which the invention pertains, unless otherwise specifically defined or stated herein. Methods, materials, and examples described herein are illustrative only and are not intended to be necessarily limiting. Although methods or/and materials equivalent or similar to those described herein can be used in practicing or/and testing embodiments of the invention, exemplary methods or/and materials are described below. In case of conflict, the patent specification, including definitions, will control.

BRIEF DESCRIPTION OF THE SEVERAL VIEWS OF THE DRAWINGS

Some embodiments of the present invention are herein described, by way of example only, with reference to the accompanying drawings and image. With specific reference now to the drawings and image in detail, it is stressed that the particulars shown are by way of example and for purposes of illustrative description of some embodiments of the present invention. In this regard, the description taken together with the accompanying drawings make apparent to those skilled in the art how some embodiments of the present invention may be practiced.

In the drawings:

FIGS. 1A-1C schematically illustrate an exemplary dual tip hemodialysis catheter, as an exemplary hemodialysis catheter having corrugated tips, in accordance with some embodiments of the invention;

FIGS. 2A-2E are schematic side views of a distal portion of an exemplary hemodialysis catheter with corrugated tips, in accordance with some embodiments of the invention;

DESCRIPTION OF SPECIFIC EMBODIMENTS OF THE INVENTION

Figure 3A:
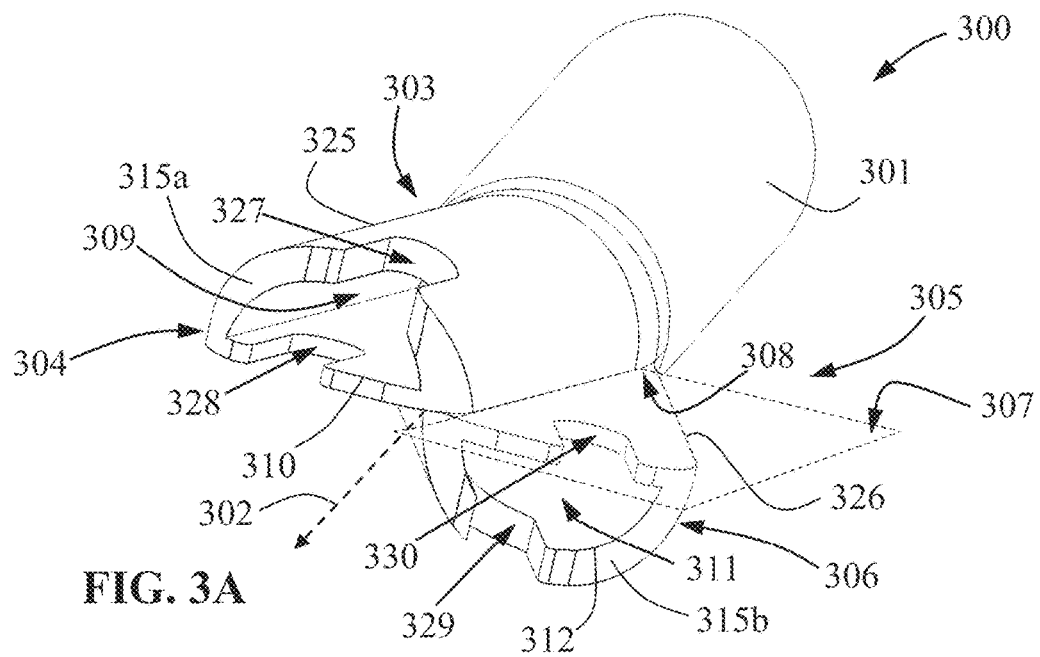
FIGS. 3A-3C schematically illustrate an exemplary hemodialysis catheter with corrugated tips, in accordance with some embodiments of the invention.

The present invention, in some embodiments thereof, relates to medical catheter apparatus, and more particularly, but not exclusively, to dialysis catheters having a dual or split tip. In exemplary embodiments of the present invention, the herein disclosed dialysis catheter corresponds to a dual (split) tip hemodialysis catheter having corrugated tips.

In exemplary embodiments, the hemodialysis catheter includes an elongated body extending along a longitudinal axis, first and second distal end regions terminating in first and second tips opened to first and second lumens that continuously extend along both the elongated body and the respective first and second distal end regions. Each tip includes a tip edge extending from tip tubular wall and surrounding tip opening. Each tip tubular wall is part of a corrugated configuration, and has at least two grooves, including outer and inner grooves, merging into the tip edge. Grooves may have same or different lengths, widths, or/and spatial configurations. Distal end regions may be elastic and configured to have a non-stressed form when divergent, via diverging angles, from the elongated body longitudinal axis. Distal end regions may be rotationally symmetric relative to the longitudinal axis. Distal end regions may be separated from each other along a splitting plane adjacent to a junction, optionally, a median plane adjacent to the junction and perpendicular to the longitudinal axis. Distal end regions may be parallel to the splitting plane.

In exemplary embodiments, when the hemodialysis catheter is in a non-stressed form, the tip openings are oriented in opposite directions relative to each other and away from the longitudinal axis. In exemplary embodiments, each tip includes a tip extension, an inner wall surface extending along the tip extension, and a hollow outer surface, whereby the inner wall surface and the hollow outer surface merge into a corrugated form having alternating grooves and ridges along the distal end of the tip extension. When the hollow outer surface is fully covered and the inner wall surface is at least partially uncovered, the hemodialysis catheter facilitates active lateral fluid traversability therethrough. When the hollow outer surface is at least partially uncovered and the inner wall surface is fully covered, the hemodialysis catheter facilitates active frontal fluid traversability therethrough.

In exemplary embodiments of the present invention, the hemodialysis catheter with corrugated tips includes particular structural features that are effective in preventing, or at least diminishing, blockage of hemodialysis lumens and blood recirculation openings associated with employing hemodialysis treatment systems. Such effectiveness may be highly advantageous compared to, and solve problems associated with, known hemodialysis catheters and uses thereof.

The term "corrugated", as used herein, in a non-limiting manner, refers to a shape having alternating grooves and ridges, optionally, parallel to each other. In some particular exemplary embodiments of the herein disclosed invention, the grooves and ridges are configured on the wall of a corrugated tip of an exemplary catheter and are opened to an end portion (e.g., an edge) of the corrugated tip. In some particular exemplary embodiments, the grooves and ridges are parallel to the longitudinal axis of the corrugated tip. The ridges or/and grooves may have different sizes or shapes. Grooves may be similar or different in shape or/and size, and ridges may be similar or different in shape or/and size. Alternating grooves and ridges may be similar or different in shape or/and size.

The term "ridge", as used herein, in a non-limiting manner, refers to any relatively raised surface or border of the edge of a corrugated tip of an exemplary catheter of the invention. In some such embodiments, a ridge may also relate to any surface or border of the corrugated edge in between two consecutive grooves around the tip edge.

The term "groove", as used herein, in a non-limiting manner, refers to any relatively shallow surface or border of the edge of a corrugated tip of an exemplary catheter of the invention. In some such embodiments, a groove may also relate to any surface or border of the corrugated edge in between two consecutive ridges around the tip edge. Any opening on a wall surrounding the catheter tip, that is also opened to the edge of the catheter tip, can also be considered as a groove within the scope of the herein disclosed invention.

The term "slit", as used herein, in a non-limiting manner, refers to a groove having a relatively narrow and long groove, optionally, and particularly, to such grooves having straight or/and parallel side borders.

For purposes of better understanding embodiments of the present invention, in the following illustrative description thereof, reference is made to the figures. Throughout the following description and accompanying drawings, same reference numbers refer to same components, elements, or features. It is to be understood that the invention is not necessarily limited in its application to any particular sequential ordering of method steps or procedures, or to particular details of construction or/and arrangement of device, apparatus, or/and system components, set forth in the following illustrative description. The invention is capable of other embodiments or of being practiced or carried out in various ways.

Referring now to the drawings, FIGS. 1A-1C schematically illustrate an exemplary dual tip hemodialysis catheter 100, as an exemplary hemodialysis catheter having corrugated tips. Set forth below are descriptions of a variety of exemplary embodiments and geometrical configurations of the distal portions of the herein disclosed hemodialysis catheter having a corrugated tip. Catheter 100 is made of flexible material in order that it can be pushed, pulled, or stretched into a wide variety of configurations. Catheter 100 includes an elongated body 110 enclosing a first lumen 112 and a second lumen 113 that is isolated from first lumen 112. First lumen 112 defines a first lumen axis 114, and second lumen 113 defines a second lumen axis 115, each is centrally located within and extending along the length of each corresponding lumen.

Catheter 100 is further defined by a longitudinal axis 116 centrally located in the elongated body 110. Although the term "centrally located" should be clear to those in the art, for absence of doubt, for each lumen this means at the centroid of the cross sectional shape perpendicular to lumen extent (such as shown in FIG. 1B) as defined by the inner surface of the wall forming the lumens. For the catheter as a whole this means at the centroid of the cross sectional shape perpendicular to lumen extent (such as shown in FIG. 1B) as defined by the outer surface of the elongated body 110. Optionally, and as illustrated schematically, elongated body 110 holds both lumens 112 and 113 aligned and unsplit or merged along the longitudinal axis 116 up to a junction 117 (optionally, in a form of a splitting point or splitting line). At junction 117, elongated body 110 splits into a first distal end region 118 and a second distal end region 119. First distal end region 118 terminates in a first tip 120 opened to first lumen 112 which extends continuously along both elongated body 110 (along the unsplit length) and first distal end region 118, and second distal end region 119 terminates in a second tip 121 opened to second lumen 113 which extends continuously along both elongated body 110 and second distal end region 119.

First and second distal end regions 118 and 119 split from a unitary form of elongated body 110 at junction 117 such that their walls are longitudinally split from each other relatively is to a singular splitting plane, for example (and as shown) a median plane 15, in a Cartesian coordinate system, which, optionally, includes or/and extends from longitudinal axis 116. Optionally and alternatively, both walls are split relatively to longitudinal axis 135 and not relatively to the median plane 150. Optionally, first distal end region 118 and second distal end region 119 extend distally substantially the same from junction 117 such that they form rotational symmetry relative to longitudinal axis 116. Unlike nonsymmetrical split tip dialysis catheters having distal end regions of different lengths, for example, symmetrical hemodialysis catheter like catheter 100 are believed to diminish the degree of unwanted dialyzed blood recirculation as may possibly occur between an upstream positioned lumen and a downstream positioned lumen.

FIG. 1B schematically illustrates a cross section of the merged portion of catheter body 110 formed as a single double-lumen catheter portion in which lumens 112 and 113 are abutting and sharing a single separating wall; nevertheless this should be considered one of many alternative exemplary configurations; other possible configurations may include different multiple-lumen shapes or any connection or adjunction (e.g., by welding, gluing or otherwise) along a surface, a line or/and points of contact between two or more single-lumen catheters. The embodiment of FIG. 1 as illustrated by FIG. 1B is known as a "Double-D" type catheter. Split or dual tip Double-D type catheter assemblies are characterized by two approximately semi-circular lumens with adjacent flat sides defined by a centrally positioned substantially linear wall. The outer circumference of the catheter assembly in the merged portion is typically of approximately circular cross section. As shown in FIG. 1, when formed into a split or dual tip, the two lumens are separated (e.g., by cutting) through and along the shared centrally positioned substantially linear wall. The direction of the splitting line (Median Plane 150) is therefore the same as the direction of the extent of the central wall in the junction portion of catheter 100.

For Double-D type catheters, the angle of separation of the two lumens may be a dihedral angle formed at their junction by the intersection of the planes defined by the inner planar surfaces of the two lumens. Catheter 100 has minimal dihedral angle in order to diminish possibility of entrapping clots or forming emboli at or adjacent junction 116. FIG. 1C, which illustrates the distal end of catheter 100, shows an exemplary embodiment in which the dihedral angle is null or insignificantly small since that inner walls of first and second distal end regions 118 and 119 are kept parallel with the splitting plane (Median Plane 1Q) or/and are not forming a gap along the Transverse Plane 16Q (being orthogonal to the Median Plane 150 in a single Cartesian system).

Elongated body 110 has a proximal end region 122 which includes a first proximal hub or port 123, and a second proximal end region 124 which includes a second proximal hub or port 125, such that first lumen 112 is opened at the first proximal port 123 and second lumen 113 is opened at the second proximal port 125.

Catheter 100 is configured to connect with a hemodialysis machine (connection can be facilitated via ports 123 and 125) such that one lumen can be used to deliver oxygenated blood into the cardiovascular system and the other lumen can be used to draw blood therefrom, while occasionally the blood circulation may be reversed between these two lumens. First lumen 112 and second lumen 113 are independent and sealed from each other, so as to facilitate simultaneous and oppositely directed flow through the first and second lumens 112 and 113, respectively.

First distal end region 118 and second distal end region 119 may be substantially pliant to conform (optionally, juxtaposingly) to boundaries of a hosting vessel lumen. Optionally and alternatively, first distal end region 118 and second distal end region 119 are substantially elastic or rigid such that first tip 120 and second tip 121 are provided in a predetermined distance or/and relative positioning upon deployment. In some embodiments, first distal end region 118 and second distal end region 119 are formed in a rotational symmetry by overall size and shape or/and openings size, shape or/and distribution, one with the other, relatively to longitudinal axis 116. Optionally and additionally, first distal end region 118 and second distal end region 119 are distanced similarly about the Transverse Plane 160 or/and optionally, distanced similarly about the median plane 150.

Catheter 100 includes distal openings for local blood dispersion and collection, distributed on distal end regions 118 and 119 or/and at first and second tips 120 and 121, while maintaining rotational symmetry around longitudinal axis 116. In some embodiments, and as shown, first distal end region 118 and second distal end region 119 are rotationally symmetric yet asymmetric (i.e., are not mirrored), and, as in this example, optionally, inverted, with respect to the Median Plane 15, in order to minimize potential unwanted recirculation of dialyzed blood between adjacent openings. A first forward opening 126, opened to first lumen 112 at first tip 120, is shaped such to direct flow passing therethrough in direction of first lumen axis 114. Likewise, a second forward opening 127 is shaped such to direct flow passing therethrough in a direction of second lumen axis 115, being nonintersecting with, and optionally, parallel to, the flow via first forward opening 126 yet opposite in direction thereto.

In order to avoid potential flow occlusion in case of choking of any of the forward openings, lateral grooves (optionally in a form of slits) are provided, situated distally to the forward openings and merging into the edges of the tips surrounding the forward openings. As shown, each of first and second tips 120 and 121 may include a number of groves or slits, including an inner groove 128 and an outer groove 129.

FIGS. 2A-2E are schematic side views of a distal portion of an exemplary hemodialysis catheter 210 with corrugated tips, which is an exemplary variation of catheter 100. Unless otherwise specified, such as describing a catheter forced to align using aligning means, the geometrical configurations described herein are the configurations that the herein disclosed hemodialysis catheter naturally takes due to its inherent construction and, material properties and characteristics, when the distal portion is in a "relaxed" or "non-stressed" state. Hemodialysis catheter 210 includes an elongated body 211 extending along a longitudinal axis 212, a first distal end region 213 terminating in a first tip 214, and a second distal end region 215 terminating in a second tip 216. The first and second distal end regions 213 and 215 are separated with each other adjacent a junction 218. First distal end region 213 encloses a first lumen 219 opened to a first tip opening 220 provided at the first tip 214, and second distal end region 215 encloses a second lumen 221 opened to a second tip opening 222 provided at the second tip 216. First lumen 219 and second lumen 221 are independent and sealed from each other, so as to facilitate simultaneous and oppositely directed flow through first and second lumens 219 and 221, as indicated by the arrows labeled 'BLOOD FLOW IN 250' and 'BLOOD FLOW OUT 260,' respectively, as required for effecting blood circulation.

Hemodialysis catheter 210 is shown at a fully deployed (relaxed or non-stressed) form in which the tips openings 220 and 222 are firmly oriented to opposite directions one with each other and away from longitudinal axis 212. Each the first and second tips 214 and 216 includes a tip length 223, an inner wall 224 surface extending along the tip length 223, and a hollow outer surface 225, as shown in FIG. 1E, which is a frontal view of first tip 214. Inner wall surface 224 and hollow outer surface 225 merge into a corrugated form 226 having alternating grooves 227 and ridges 228 along distal end of the tip length 223.

In exemplary embodiments, for example, as shown in FIG. 2C, when hollow outer surface 225 is fully covered and inner wall surface 224 is at least partially uncovered, hemodialysis catheter 210 facilitates active lateral fluid traversability therethrough. In FIG. 2C, such exemplary active lateral fluid flow is indicated by the arrows labeled 'LATERAL IN-FLOW 250a' and 'LATERAL OUT-FLOW 260a'. In exemplary embodiments, for example, as shown in FIG. 2D, when hollow outer surface 225 is at least partially uncovered and inner wall surface 224 is fully covered, hemodialysis catheter 210 facilitates active frontal fluid traversability therethrough. In FIG. 2D, is such exemplary active frontal fluid flow is indicated by the arrows labeled 'FRONTAL IN-FLOW 250b' and 'FRONTAL OUT-FLOW 260b'. Hemodialysis catheter 210 excludes any lateral openings at any of first 213 and second 215 end regions other than the grooves and ridges.

Hemodialysis catheter 210 at its fully deployed (relaxed or non-stressed) form, has first distal end region 213 and second distal end region 215 rotationally symmetric one with the other relative to longitudinal axis 212 including grooves 227 and ridges 228 being distributed and shaped in accordance with the rotational symmetry.

Figure 3B:
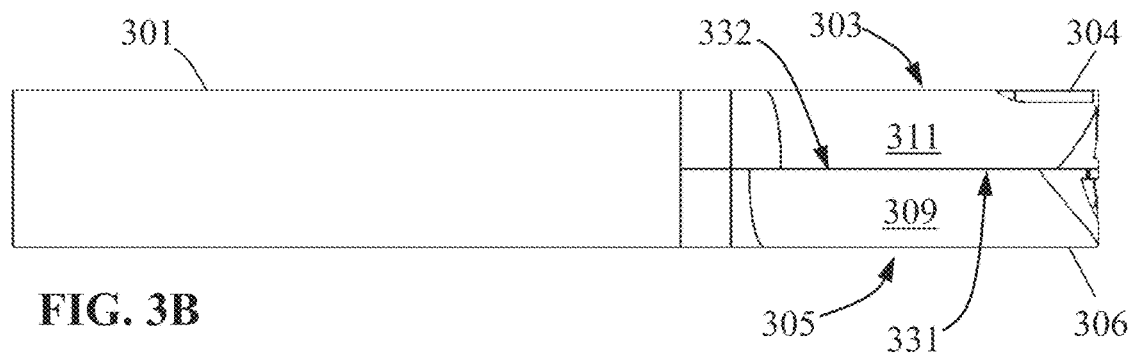
Figure 3C:
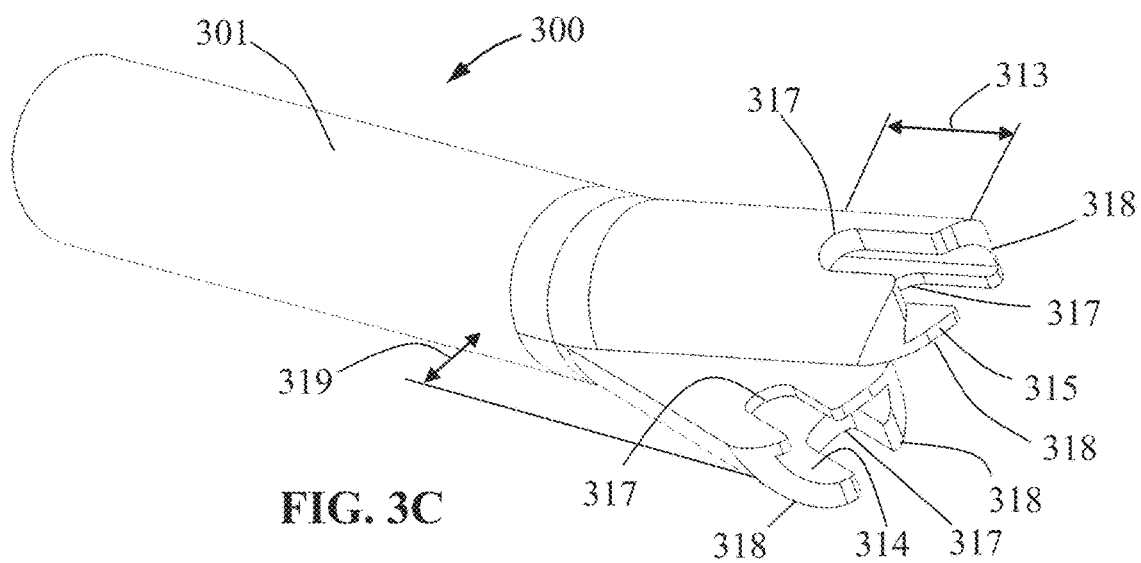
Figure 4A:
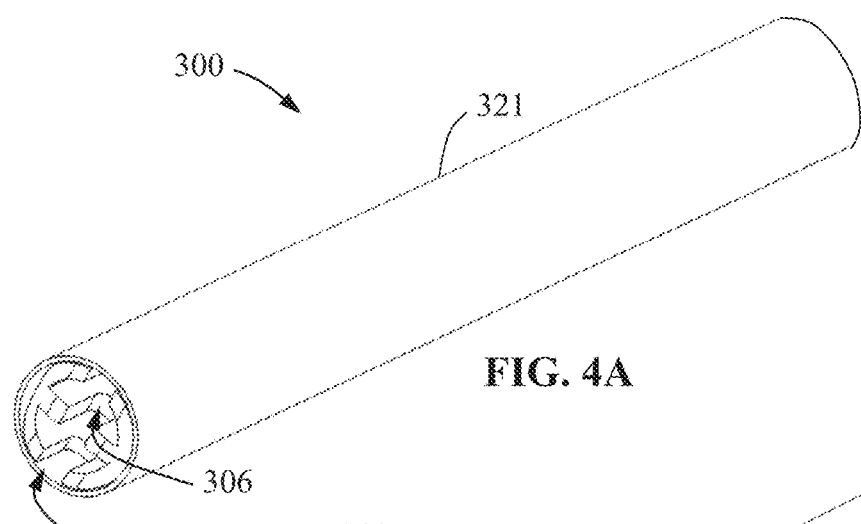
FIGS. 4A-4C schematically illustrate the exemplary hemodialysis catheter of FIGS. 3A-3C, before deployment (FIGS. 4A, 4B) and after deployment (FIG. 4C), in accordance with some embodiments of the invention.
Figure 4B:
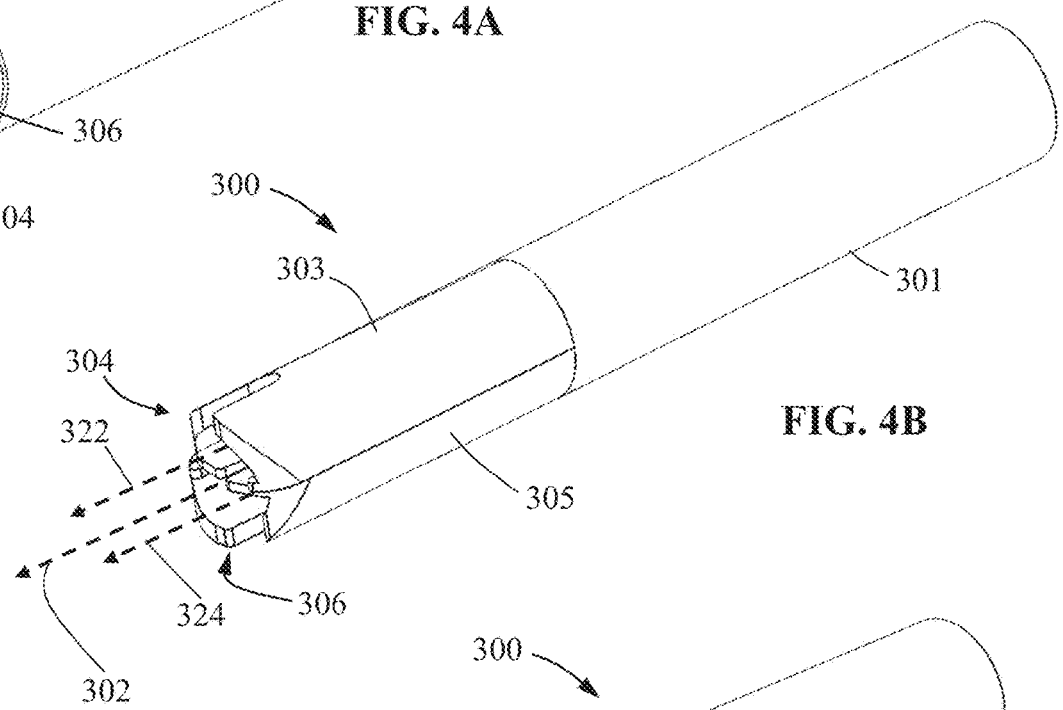
Figure 4C:
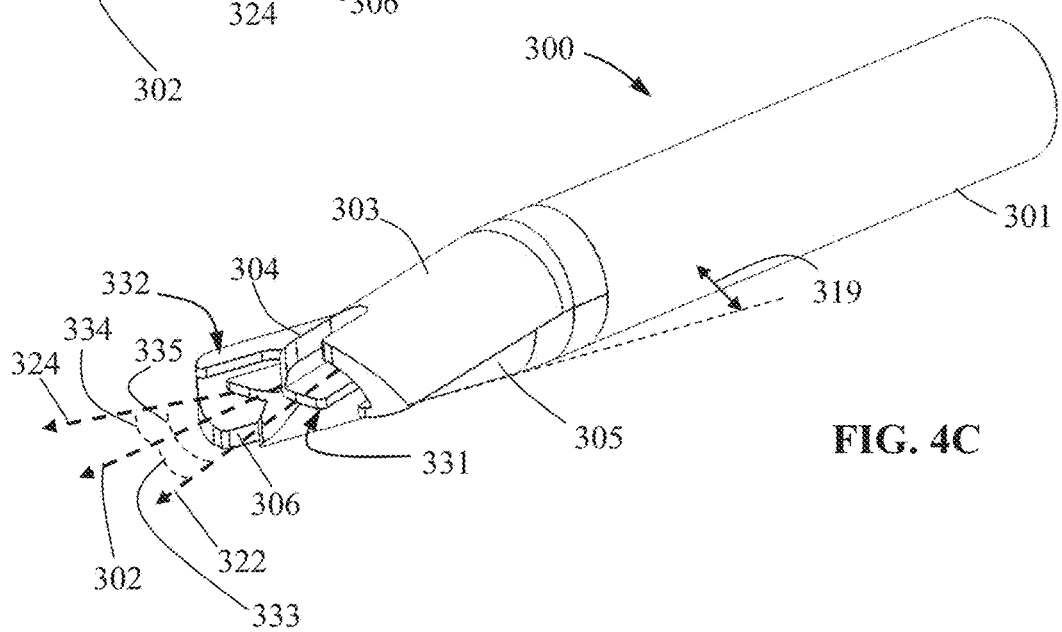

Reference is now made to FIGS. 3A-3C and 4A-4C. FIGS. 3A-3C which schematically illustrate an exemplary hemodialysis catheter 300 with a corrugated distal end, as defined above, shown only with a distal end thereof. FIGS. 4A-4C highlight the distal end of hemodialysis catheter 300 before deployment (FIGS. 4A, 4B) and after deployment (FIG. 4C). Catheter 300 can be considered another exemplary variation of catheter 100 with similarity in structure or/and function to parts and elements of catheter 100 or/and catheter 200.

Hemodialysis catheter 300 includes an elongated body 301 (shown only with a front segment thereof) extending along a longitudinal axis 302, a first distal end region 303 terminating in a first tip 304, and a second distal end region 305 terminating in a second tip 306. The first 303 and second 305 distal end regions are separated with each other along a splitting plane 307 adjacent a junction 308. First distal end region 303 encloses a first lumen 309 opened to a first tip opening 310 provided at the first tip 304, and second distal end region 305 encloses a second lumen 311 opened to a second tip opening 312 provided at the second tip 306. First lumen 309 and second lumen 311 are independent and sealed from each other, so as to facilitate simultaneous and oppositely directed flow through first and second lumens 309 and 311, respectively, as required for effecting blood circulation.

Hemodialysis catheter 300 is shown at a fully deployed (relaxed or non-stressed) form in which the tips openings 310 and 312 are oriented to opposite directions one with each other and away from longitudinal axis 302. Each the first 304 and second 306 tips includes a tip length 313, an inner wall 314 surface extending along the tip length 313, and a tip edge 315. Inner wall surface 314 and tip edge 315 merge into a corrugated form having alternating grooves 317 and ridges 318 along distal end of the tip length 313. This way facilitates active 1o lateral fluid traversability, if tip edge 315 is fully covered and inner wall surface 311 is at least partially uncovered (as previously demonstrated in FIG. 2C), and active frontal fluid traversability, if tip edge 315 is at least partially uncovered and inner wall surface 314 is fully covered (as previously demonstrated in FIG. 2D). Hemodialysis catheter 300 excludes any lateral openings at any of first 303 and second 305 end regions.

Hemodialysis catheter 300 at its fully deployed (relaxed or non-stressed) form, has first distal end region 303 and second distal end region 305 rotationally symmetric one with the other relative to longitudinal axis 302 including grooves 327 and ridges 328 being distributed and shaped in accordance with the rotational symmetry.

According to some embodiments of the invention, elongated body 301 is elastically shapeable from a confined form, whereby the first 303 and second 305 end regions are forced to approximate each other within restricting boundaries, to the fully deployed form, whereby the first 303 and 305 second end regions are unconfined. Hemodialysis catheter 300 may be provided with removable aligning means 321 that facilitate alignment of the first distal end region 303 together with the second distal end region 305 to longitudinal axis 302, as shown in FIG. 4A. Upon removal of aligning means 321, as shown in FIGS. 4B and 4C, first distal end region 303 and second distal end region 305 voluntarily slide against each other, such as in a scissor like movement, along splitting plane 307, up to the fully deployed form (FIG. 4C).

In some embodiments, first lumen 309 has a first tip longitudinal axis 322 extending therealong, and second lumen 311 has a second tip longitudinal axis 324 extending therealong. Optionally, when catheter 300 is in the fully deployed form (e.g., in the non-stressed form or a less stressed form than when confined with alignment means such as means 321), first and second tip longitudinal axes 322 and 324 are parallel along a proximal portion of the catheter and diverge over a distal portion of the catheter. First and second tip longitudinal axes 322 and 324 define the splitting plane 307 being, optionally, a median or transverse plane including both the first and second tip longitudinal axes in the proximal portion of the catheter.

Each first and second tips 304 and 306 diverges from the elongated body and has a protrusion length 319 in a range of between 5 mm and 35 mm, and diverges from elongated body 301 relative to longitudinal axis 302. In some embodiments, hemodialysis catheter 300 has a maximal outer diameter changeable from a range of between 4 mm and 6 mm to a range of between 7 mm and 30 mm when in the fully deployed form.

In some embodiments, elongated body 301 is 10 cm to 50 cm long, optionally, about 16 cm to about 45 cm, with designated maximal length inside a subject body to be about 300 cm or less, optionally, about 40 cm or less, optionally, about 36 cm. Optionally, lumens 309 and 311 are between 2 and 10 mm in diameter, optionally, about 4 mm to about 6 mm. In some embodiments, openings 310 and 312 are substantially similar in size to lumens 309 and 311, although openings size may be smaller or greater. In some embodiments, any of tip length 313, width of grooves 317, length of grooves 317, width of ridges 318, and length of ridges 318 are in a range between 1 and 8 mm, optionally, between 2 mm and 5 mm. Tip length 313, width of grooves 317, length of grooves 317, width of ridges 318, and length of ridges 318 may be of same or different sizes, or in any combination thereof. Catheter 300 may be made from medical or/and implant grade material having chosen elastic and stiffness properties, and may be formed from polymeric materials such as polyurethane, including polycarbonate-based thermoplastic polyurethanes (such as Carbothane™ TPU, by The Lubrizol Corporation, Wickliffe, Ohio USA) and silicone.

First distal end region 303 terminates in first tip 304 being opened to first lumen 309. First lumen 309 extends continuously along both elongated body 301 and first distal end region 303. Second distal end region 305 terminates in second tip 306 being opened to second lumen 311. Second lumen 311 extends continuously along both elongated body 301 and second distal end region 305. First tip 304 includes a first tip edge 315a that extends from a first tip tubular wall 325, and surrounding first tip opening 310. Second tip 306 includes a second tip edge 315b that extends from a second tip tubular wall 326, and surrounding second tip opening 312. First tip tubular wall 325 includes at least two grooves 317 merging into first tip edge 315a, including a first outer groove 327 and a first inner groove 328. Likewise, second tip tubular wall 326 includes at least two grooves 317 merging into second tip edge 315b, including a second outer groove 329 and a second inner groove 330.

First inner groove 328 extends along a first inner side 331 of first distal end region 303 and second inner groove 330 extends along a second inner side 332 of second distal end region 305. As such, first inner side 331 is at least partially in contact with second inner side 332. As shown, first inner groove 328 opposes first outer 327 groove or/and second inner groove 330 opposes second outer groove 329. In some embodiments, each groove 317 of first and second tip tubular walls 325 and 326 has length 313 of at least 2 mm, optionally, particularly ranging between 2 mm and 3 mm. In some embodiments, each groove 317 of first and second tip tubular walls 325 and 326 has width of at least 1 mm, optionally, particularly ranging between 1 mm and 1.5 mm. The grooves 317 may be identical in length or/and width or they may vary.

In some embodiments, at least one of first and second distal end regions 303 and 305 is elastic and configured to have a non-stressed form when first distal end region 303 diverges from longitudinal axis 302 via a first diverging angle 333 or/and second distal end region 305 diverges from longitudinal axis via a second diverging angle 334 (as shown in FIG. 4C, for example). First diverging angle 333 is equal and directionally opposite to second diverging angle 334, relative to the longitudinal axis 302, thereby forming together a total diverging angle 335 defined by and spanning between first and second distal end regions 303 and 305. Total diverging angle 335 optionally, ranges between 5° and 50°, optionally, particularly, between 20° and 30°. First inner groove 328 is convergent with, or crosses, second inner groove 330 when first and second distal end regions 303 and 305 are aligned with longitudinal axis 302 (as shown in FIGS. 4A and 4B, for example). In some embodiments, first inner groove 328 is fully separated from second inner groove 330 when first or/and second distal end regions 303 and 305 is/are in the non-stressed form.

First and second distal end regions 303 and 305 and (exemplary first and second inner) grooves 317 are rotationally symmetric relative to longitudinal axis 302, and first tip 304 extends in same length as second tip 306, relative to junction 308. First and second distal end regions 303 and 305 being separated with each other along splitting plane 307, which is optionally, a median plane. First and second distal end regions 303 and 305 are substantially parallel to splitting plane 307. First tip tubular wall 325 has a first flat surface (e.g., first inner side 331) and second tip tubular wall 326 has a second flat surface (e.g., second inner side 332) facing the first flat surface. The first flat surface or/and second flat surface is parallel to splitting plane 307.

At least one of first inner groove 328 and first outer groove 327 is in a form of a straight slit extending parallel to first tip longitudinal axis 322 of first distal end portion 303, and, at least one of second inner groove 330 and second outer groove 329 is in a form of a straight slit extending parallel to second tip longitudinal axis 324 of second distal end portion 305. In exemplary embodiments, first and second tips 304 and 306 have a blunt form.

Figure 5A:
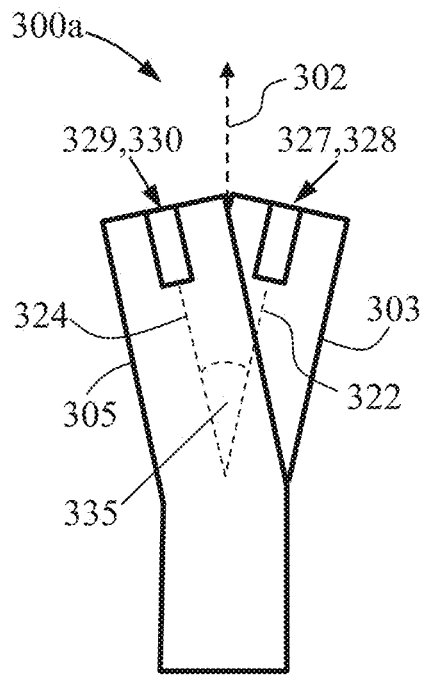
FIGS. 5A-5D schematically illustrate exemplary variations of the hemodialysis catheter, highlighting different configurations of the corrugated tip and features thereof, in accordance with some embodiments of the invention.

FIGS. 5A-5D schematically illustrate exemplary variations of the hemodialysis catheter with corrugated tips, for example, hemodialysis catheter 300. In all these variations, the distal end portions 303 and 305 are rotationally symmetric around longitudinal axis 302, and are of same length until corresponding tips thereof. FIG. 5A shows a first exemplary variation 300a of catheter 300, wherein first inner groove 328 is identical in length to first outer groove 327 or/and second inner groove 330 is identical in length to second outer groove 329. As shown, all grooves 317 are 3 mm in length and 1.3 mm wide. Total length of first and second distal end portions 303 and 305 is 12 mm. Both inner and outer grooves extend along symmetry line of each corresponding distal end portion. Total diverging angle 335 is 24°. As shown, first inner groove 328 and first outer groove 327 are positioned 180 degrees circumferentially away from each other relative to first tip longitudinal axis 322. Likewise, second inner groove 330 and second outer groove 329 are positioned 180 degrees circumferentially away from each other relative to second tip longitudinal axis 324.

Figure 5B:
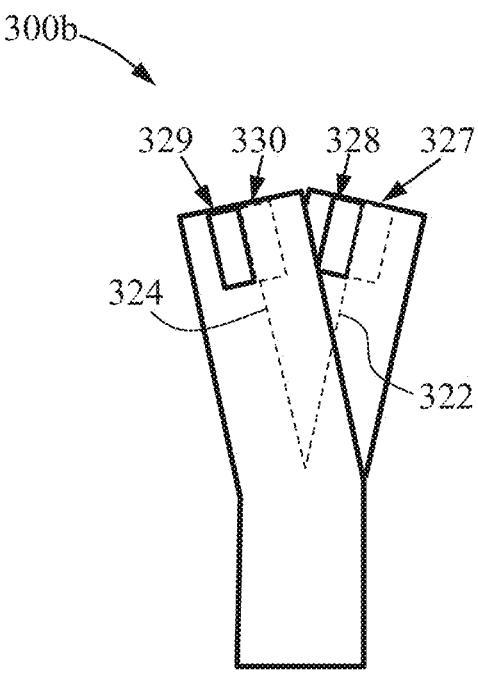

FIG. 5B shows a second exemplary variation 300b of catheter 300, wherein one of first inner groove 328 and first outer groove 327 is positioned closer than the other to first tip longitudinal axis 322. Likewise, one of second inner groove 330 and second outer groove 329 is positioned closer than the other to second tip longitudinal axis 324. In some such embodiments, first inner groove 328 and first outer groove 327 are situated on opposite sides of symmetry line of first distal end portion 303. Likewise, second inner groove 330 and second outer groove 329 are situated on opposite sides of symmetry line of second distal end portion 305. Dimensions of exemplary variation 300b of catheter 300 are the same as the dimensions of exemplary variation 300a of catheter 300.

Figure 5C:
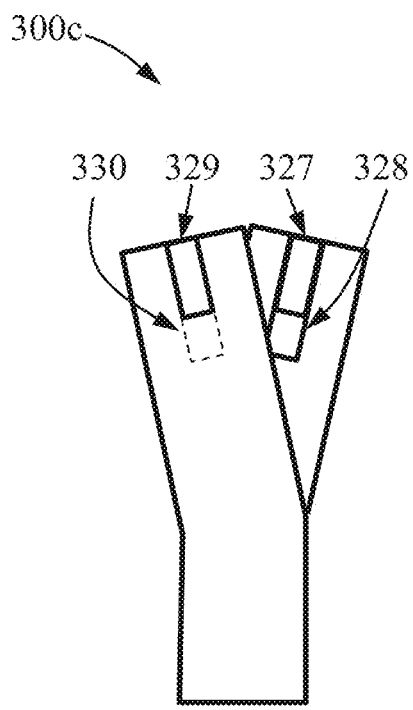

FIG. 5C shows a third exemplary variation 300c of catheter 300, wherein length of first inner groove 328 is greater than length of first outer groove 327, and length of second inner groove 330 is greater than length of second outer groove 329. For example, first and second inner grooves 328 and 330 are 3 mm to 6 mm, optionally, about 5 mm, in length, while first and second outer grooves 327 and 329 are 1 mm to 3 mm, optionally, about 3 mm, in length. Total length of first and second distal end portions 303 and 305 is about 11 mm. Both inner and outer grooves extend along symmetry line of each corresponding distal end portion. Total diverging angle 335 is about 22.5°.

Figure 5D:
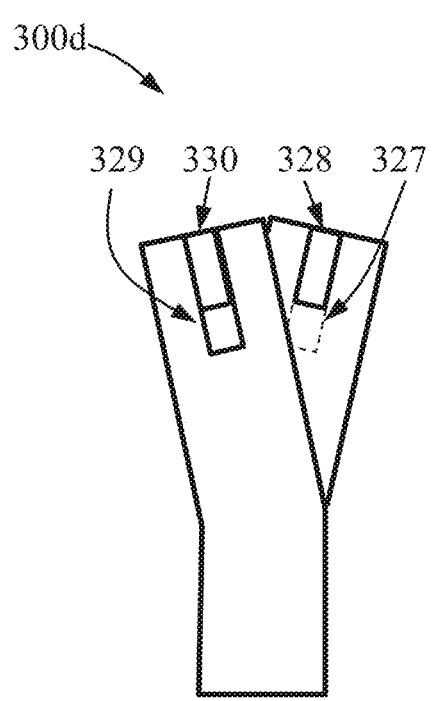

FIG. 5D shows a fourth exemplary variation 300d of catheter 300, wherein length of first inner groove 328 is smaller than length of first outer groove 327, and length of second inner groove 330 is smaller than length of second outer groove 329. For example, first and second inner grooves 328 and 330 are 1 mm to 3 mm, optionally, about 3 mm, in length, while first and second outer grooves 327 and 329 are 3 mm to 6 mm, optionally, about 5 mm, in length. Rest of dimensions are same as in exemplary variation 300c.

In all three variations, elongated body 301 is 4.95 mm in diameter, with wall thickness of 0.64 mm and inner wall width is 0.86 mm, which is then separated in half when splitting to first and second distal end portions 303 and 305.

Figure 6:
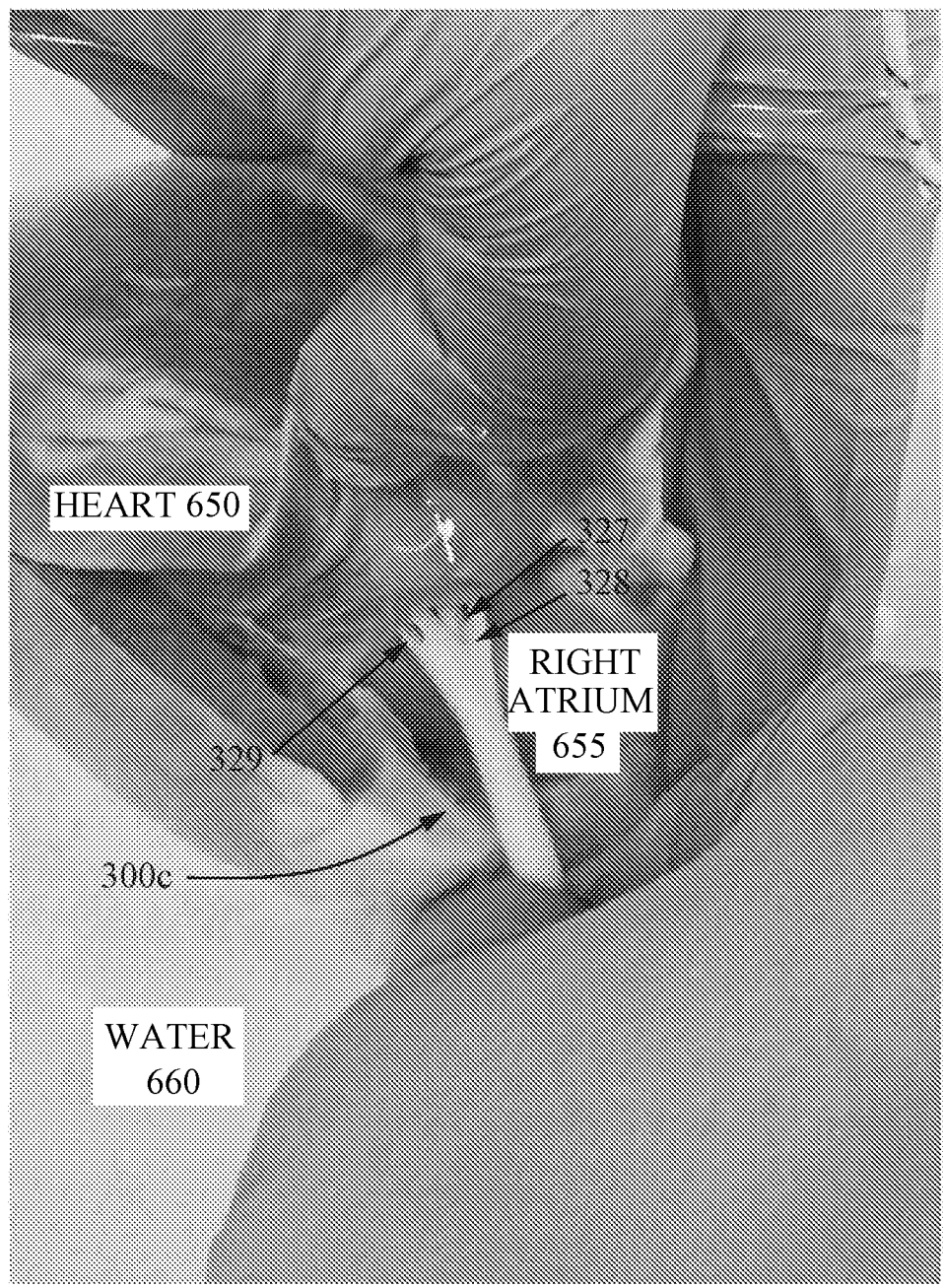
FIG. 6 is a photograph of an actual experimental scenario involving implementation of an exemplary prototype of the exemplary hemodialysis catheter of FIG. 5C, in accordance with some embodiments of the invention.

FIG. 6 is a photograph of an actual experimental scenario involving implementation of an exemplary prototype of the exemplary hemodialysis catheter 300c shown in FIG. 5C. The heart 650 of a cow (as an exemplary bodily organ) was placed in a water 660 filled container pre-heated to 37° C. The right atrium 655 of the heart 650 was cut in order to enable positioning of the distal end of catheter 300c under direct sight. The first lumen of the catheter was operatively connected to a first pump set to draw water 660 via the lumen opening at a rate of about 600 ml/min, while the second lumen was operatively connected to a second pump for delivering water 660 back into the water filled container. While heart 650 and catheter distal end were submerged in the water 660 and the pump was on, the tips of the catheter were pressed against the tissue wall in the right atrium 655 at is different angles and positions. In all cases, at least one groove in each catheter distal end portion (and lumen) was opened (unobstructed) sufficiently to facilitate effective water delivery via both lumens in both directions. These experimental results provide evidence of at least one of the advantages of using the herein disclosed corrugated (slit) tip structure in a hemodialysis catheter configured for placement in a bodily organ, such as the heart 650. During actual use, the hemodialysis catheter was highly effective in preventing positional occlusion in at least one of the catheter lumens.

Each of the following terms written in singular grammatical form: 'a', 'an', and 'the', as used herein, means 'at least one', or 'one or more'. Use of the phrase 'one or more' herein does not alter this intended meaning of 'a', 'an', or 'the'. Accordingly, the terms 'a', 'an', and 'the', as used herein, may also refer to, and encompass, a plurality of the stated entity or object, unless otherwise specifically defined or stated herein, or, unless the context clearly dictates otherwise. For example, the phrases: 'a unit', 'a device', 'an assembly', 'a mechanism', 'a component', 'an element', and 'a step or procedure', as used herein, may also refer to, and encompass, a plurality of units, a plurality of devices, a plurality of assemblies, a plurality of mechanisms, a plurality of components, a plurality of elements, and, a plurality of steps or procedures, respectively.

Each of the following terms: 'includes', 'including', 'has', 'having', 'includes', and 'including', and, their linguistic/grammatical variants, derivatives, or/and conjugates, as used herein, means 'including, but not limited to', and is to be taken as specifying the stated component(s), feature(s), characteristic(s), parameter(s), integer(s), or step(s), and does not preclude addition of one or more additional component(s), feature(s), characteristic(s), parameter(s), integer(s), step(s), or groups thereof. Each of these terms is considered equivalent in meaning to the phrase 'consisting essentially of'.

The term 'method', as used herein, refers to steps, procedures, manners, means, or/and techniques, for accomplishing a given task including, but not limited to, those steps, procedures, manners, means, or/and techniques, either known to, or readily developed from known steps, procedures, manners, means, or/and techniques, by practitioners in the relevant field(s) of the disclosed invention.

Throughout this disclosure, a numerical value of a parameter, feature, characteristic, object, or dimension, may be stated or described in terms of a numerical range format. Such a numerical range format, as used herein, illustrates implementation of some exemplary embodiments of the invention, and does not inflexibly limit the scope of the exemplary embodiments of the invention. Accordingly, a stated or described numerical range also refers to, and encompasses, all possible sub-ranges and individual numerical values (where a numerical value may be expressed as a whole, integral, or fractional number) within that stated or described numerical range. For example, a stated or described numerical range 'from 1 to 6' also refers to, and encompasses, all possible sub-ranges, such as 'from 1 to 3', 'from 1 to 4', 'from 1 to 5', 'from 2 to 4', 'from 2 to 6', 'from 3 to 6', etc., and individual numerical values, such as '1', '1.3', '2', '2.8', '3', '3.5', '4', '4.6', '5', '5.2', and '6', within the stated or described numerical range of 'from 1 to 6'. This applies regardless of the numerical breadth, extent, or size, of the stated or described numerical range.

Moreover, for stating or describing a numerical range, the phrase 'in a range of between about a first numerical value and about a second numerical value', is considered equivalent to, and meaning the same as, the phrase 'in a range of from about a first numerical value to about a second numerical value', and, thus, the two equivalently meaning phrases may be used interchangeably. For example, for stating or describing the numerical range of room temperature, the phrase 'room temperature refers to a temperature in a range of between about 20° C. and about 25° C.', and is considered equivalent to, and meaning the same as, the phrase 'room temperature refers to a temperature in a range of from about 20° C. to about 25° C.'.

The term 'about', as used herein, refers to ±10% of the stated numerical value.

It is to be fully understood that certain aspects, characteristics, and features, of the invention, which are, for clarity, illustratively described and presented in the context or format of a plurality of separate embodiments, may also be illustratively described and presented in any suitable combination or sub-combination in the context or format of a single embodiment. Conversely, various aspects, characteristics, and features, of the invention which are illustratively described and presented in combination or sub-combination in the context or format of a single embodiment, may also be illustratively described and presented in the context or format of a plurality of separate embodiments.

Although the invention has been illustratively described and presented by way of specific exemplary embodiments, and examples thereof, it is evident that many alternatives, modifications, or/and variations, thereof, will be apparent to those skilled in the art. Accordingly, it is intended that all such alternatives, modifications, or/and variations, fall within the spirit of, and are encompassed by, the broad scope of the appended claims.

All publications, patents, and or/and patent applications, cited or referred to in this disclosure are herein incorporated in their entirety by reference into the specification, to the same extent as if each individual publication, patent, or/and patent application, was specifically and individually indicated to be incorporated herein by reference. In addition, citation or identification of any reference in this specification shall not be construed or understood as an admission that such reference represents or corresponds to prior art of the present invention. To the extent that section headings are used, they should not be construed as necessarily limiting.

What is claimed is:

1. A hemodialysis catheter, comprising:
an elongated body extending along a longitudinal axis;
a first distal end region extending from the elongated body, the first distal end region terminating in a first tip, the first tip including an inner groove and an outer groove to form a corrugated first tip edge surrounding a first tip opening; and
a second distal end region extending from the elongated body, the second distal end region terminating in a second tip, the second tip including an inner groove and an outer groove to form a corrugated second tip edge surrounding a second tip opening, wherein:
the second distal end region is separated from the first distal end region along a median plane,
the longitudinal axis lies in the median plane and a transverse plane orthogonal to the median plane, and
the first distal end region and the second distal end region are designed to diverge from the transverse plane at equal and directionally opposite angles without forming a gap along the median plane.

2. The hemodialysis catheter according to claim 1, wherein said inner groove of the first tip extends along a first inner side of said first distal end region, and said inner groove of the second tip extends along a second inner side of said second distal end region, wherein said first inner side at least partially contacts said second inner side.

3. The hemodialysis catheter according to claim 1, wherein said inner groove of each of said first and second tips opposes said respective outer groove of each of said first and second tips.

4. The hemodialysis catheter according to claim 1, wherein said inner groove of each of said first and second tips has a length greater than a length of said respective outer groove of each side of said first and second tips.

5. The hemodialysis catheter according to claim 1, wherein each of said inner groove and outer groove of the first tip has a length of at least 2 mm and a width of at least 1 mm.

6. The hemodialysis catheter according to claim 1, wherein diverging angles of said first and second distal end regions, relative to said longitudinal axis, form together a total diverging angle greater than 20°.

7. The hemodialysis catheter according to claim 1, wherein a first of said inner groove provided on said first distal end region is convergent with a second of said inner groove provided on said second distal end region, when said first and second distal end regions are forced into alignment with said longitudinal axis.

8. The hemodialysis catheter according to claim 1, wherein a first of said inner groove provided on said first distal end region is fully separated from a second inner groove provided on said second distal end region.

9. The hemodialysis catheter according to claim 1, wherein said inner groove and outer groove of said first distal end region, and said inner groove and outer groove of said second distal end region are rotationally symmetric with each other relative to said longitudinal axis.

10. The hemodialysis catheter according to claim 1, wherein each of said first and second distal end regions includes a tubular wall having a flat inner surface parallel to said splitting plane.

11. The hemodialysis catheter according to claim 1, wherein each of said inner groove and said outer groove of the first tip is in a form of a straight slit.

12. The hemodialysis catheter according to claim 1, wherein said inner groove and said outer groove, in each of said first and second tips, are positioned 180 degrees circumferentially away from each other.

13. The hemodialysis catheter according to claim 1, wherein each of said first and second distal end regions has a protrusion length in a range of between 5 mm and 35 mm.

14. The hemodialysis catheter according to claim 10, wherein each of said first and second distal end regions includes a curved outer surface, wherein said flat inner surface and said curved outer surface of each of said first and second distal end regions merge into a corrugated form comprising said inner groove and outer groove of the first tip and said inner groove and outer groove of the second tip.

15. The hemodialysis catheter according to claim 10, wherein said tubular wall is sealed for allowing fluid traversability only through said first or/and second tip opening or/and one or more of said inner groove and outer groove of one or both of the first tip and the second tip.

* * * * *